United States Patent [19]  [11] Patent Number: 4,605,434
Maier  [45] Date of Patent: Aug. 12, 1986

[54] HERBICIDAL AND PLANT-GROWTH-REGULATING (2-NITRO-5-ARYLOXY-PHENYLAMINO)-ALKYLPHOSPHINE OXIDE DERIVATIVES AND COMPOSITIONS

[75] Inventor: Ludwig Maier, Arlesheim, Switzerland

[73] Assignee: CIBA-GEIGY Corporation, Ardsley, N.Y.

[21] Appl. No.: 630,131

[22] Filed: Jul. 12, 1984

[30] Foreign Application Priority Data

Jul. 20, 1983 [CH] Switzerland .................. 3989/83

[51] Int. Cl.[4] .................. C07F 9/58; C07F 9/53; A01N 51/24; A01N 51/22
[52] U.S. Cl. .................. 71/94; 71/86; 564/12; 558/385; 546/24
[58] Field of Search .................. 546/24; 564/12; 71/94, 71/86; 260/944, 945

[56] References Cited

U.S. PATENT DOCUMENTS 4,456,464  6/1984  Lee et al. .................. 71/87

FOREIGN PATENT DOCUMENTS 0079635  5/1983  European Pat. Off. .................. 71/86

*Primary Examiner*—Alan L. Rotman
*Attorney, Agent, or Firm*—Edward McC. Roberts

[57] ABSTRACT (2-Nitro-5-aryloxy-phenylamino)-alkylphosphine oxide derivatives of the formula I $$X_m \underset{Y}{\diagdown} \text{—O—} \diagdown \text{—NO}_2, \quad \underset{R^1}{\overset{R^2}{N}} \left( \underset{R^3}{\overset{|}{C}} \right)_n \overset{O}{\underset{R^5}{\overset{\|}{P}}} R^4 \quad (I)$$

wherein
X is halogen, $CF_3$, $NO_2$, CN, $CONH_2$ or $CSNH_2$,
Y is nitrogen or —CH=,
$R^1$ is hydrogen, $C_1$–$C_4$-alkyl, or aralkyl having 1–4 carbon atoms in the alkyl moiety,
$R^2$ is hydrogen or $C_1$–$C_4$-alkyl,
$R^3$ is hydrogen, $C_1$–$C_4$-alkyl, phenyl, benzyl or $C_1$–$C_4$-alkylbenzyl,
$R^4$ and $R^5$ independently of one another are each $C_1$–$C_4$-alkyl, $C_1$–$C_4$-haloalkyl, $C_2$–$C_6$-alkoxyalkyl, or aralkyl having 1–4 carbon atoms in the alkyl moiety,
m is zero to 3, and
n is 1 to 3,
have useful herbicidal properties.

26 Claims, No Drawings

HERBICIDAL AND PLANT-GROWTH-REGULATING (2-NITRO-5-ARYLOXY-PHENYLAMINO)-ALKYL-PHOSPHINE OXIDE DERIVATIVES AND COMPOSITIONS

The present invention relates to (2-nitro-5-aryloxy-phenylamino)-alkylphosphine oxide derivatives, to processes for producing them, to herbicidal and plant-growth-regulating compositions containing them, and to the use of these compounds or of compositions containing them for controlling undesirable plant growth and for regulating plant growth.

The novel compounds according to the present invention correspond to the formula I

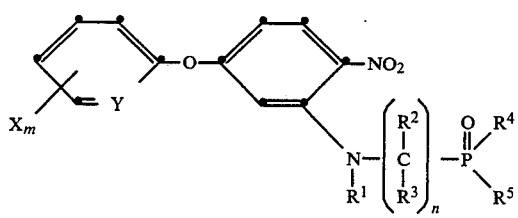

wherein
X is halogen, $CF_3$, $NO_2$, CN, $CONH_2$ or $CSNH_2$,
$Y_1$ is nitrogen or —CH=,
$R^1$ is hydrogen, $C_1$-$C_4$-alkyl, or aralkyl having 1–4 carbon atoms in the alkyl moiety,
$R^2$ is hydrogen or $C_1$-$C_4$-alkyl,
$R^3$ is hydrogen, $C_1$-$C_4$-alkyl, phenyl, benzyl or $C_1$-$C_4$-alkylbenzyl,
$R^4$ and $R^5$ independently of one another are each $C_1$-$C_4$-alkyl, $C_1$-$C_4$-haloalkyl, $C_2$-$C_6$-alkoxyalkyl, or aralkyl having 1–4 carbon atoms in the alkyl moiety,
m is zero to 3, and
n is 1 to 3.

In the definition of the formula I, alkyl as a rule is: methyl, ethyl, n-propyl or i-propyl, as well as the isomeric butyl groups. Alkyl is to be understood as being also a part of another group, for example aralkyl, haloalkyl or alkoxy.

Halogen is in general: fluorine, chlorine, bromine or iodine; preferably however it is fluorine and in particular chlorine.

Examples of aralkyl groups as defined are in general: phenylalkyl, such as benzyl, or 2-phenylethyl, 3-phenylpropyl, 1-phenylethyl, 2-phenylpropyl or 1-phenylpropyl, benzyl being preferred.

Phenyl and aralkyl groups are unsubstituted or substituted by lower alkyl groups, halogen, cyano, nitro or lower alkoxy groups. Unsubstituted phenyl or aralkyl groups are preferred.

The alkyl and alkoxy moieties in alkoxyalkyl groups each contain at most 4 carbon atoms. Preferred alkoxyalkyl groups contain as a rule all together 2 to 4 carbon atoms. Such groups are: methoxymethyl, methoxyethyl, methoxypropyl, ethoxymethyl, ethoxyethyl or propyloxymethyl.

Correspondingly, haloalkyl as a rule is: chloromethyl, dichloromethyl, trichloromethyl, 2-chloroethyl, 1,1,2,2-tetrachloroethyl, perchloroethyl, fluoromethyl, difluoromethyl, trifluoromethyl, 2,2,2-trifluoroethyl, 1,1,2,2-tetrafluoroethyl or perfluoroethyl.

The symbol n is preferably 1. When n is 2 or 3, the different groups $R^2$ and $R^3$ independently of one another have the meanings given for $R^2$ and $R^3$.

Preferred compounds of the formula I are those in which:
(a) m is 2; or
(b) X is trifluoromethyl or chlorine; or
(c) $R^1$ is hydrogen; or
(d) $R^4$ is $C_1$-$C_4$-alkyl; or
(e) $R^5$ is $C_1$-$C_4$-alkyl.

Further preference is given to the compounds of the formula I wherein Y is the —CH= group and m is 2, and the two X groups are chlorine in the 2-position and trifluoromethyl in the 4-position, respectively, $R^1$ is hydrogen, and $R^4$ and $R^5$ independently of one another are each $C_1$-$C_4$-alkyl.

Preference is likewise given to the compounds of the formula I wherein Y is nitrogen, the pyridine ring is etherified in the 2-position, m is 1, and X is trifluoromethyl in the 5-position, $R^1$ is hydrogen, and $R^4$ and $R^5$ independently of one another are each $C_1$-$C_4$-alkyl.

Particularly preferred are the compounds of the following subformulae:

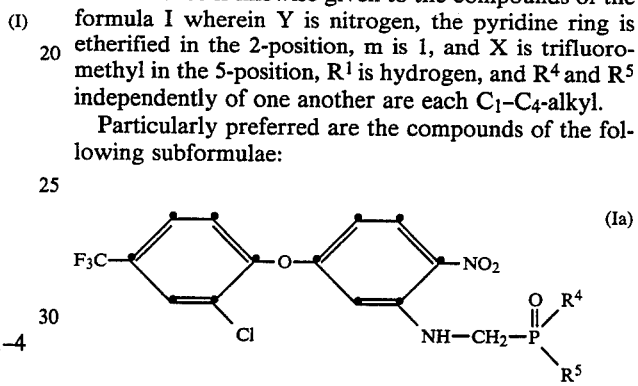

wherein $R^4$ and $R^5$ independently of one another are each methyl or ethyl;

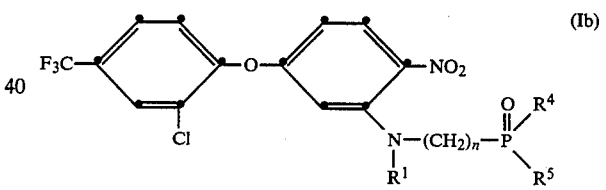

wherein $R^1$ is hydrogen, methyl, ethyl, propyl or benzyl, $R^4$ and $R^5$ independently of one another are each $C_1$-$C_4$-alkyl, and n is 1 to 3; and

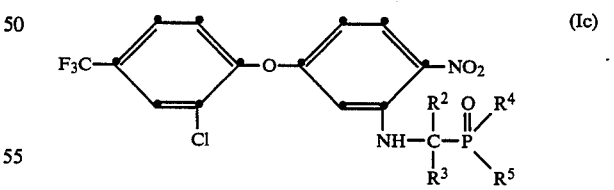

wherein $R^2$ is methyl, $R^3$ is hydrogen or methyl, and $R^4$ and $R^5$ independently of one another are each methyl or ethyl.

The following are mentioned as preferred individual compounds:
N-[2-nitro-5-(2-chloro-4-trifluoromethylphenoxy)-phenyl]-P,P-dimethylaminomethylphosphine oxide,
N-[2-nitro-5-(5-trifluoromethyl-2-pyridyloxy)-phenyl]-P,P-dimethylaminomethylphosphine oxide,
N-[2-nitro-5-(3,5-dichloro-2-pyridyloxy)-phenyl]-P,P-dimethylaminomethylphosphine oxide, N-[2-nitro-5-(2-chloro-4-trifluoromethylphenoxy)-phenyl]-P,P-diethylaminomethylphosphine oxide, N-[2-nitro-5-(2-chloro-4-trifluoromethylphenoxy)-phenyl]-P,P-dimethyl-1-aminobutylphosphine oxide, N-[2-nitro-5-(2-chloro-4-trifluoromethylphenoxy)-phenyl]-P,P-dimethyl-1--aminoethylphosphine oxide, N-[2-nitro-5-(3-chloro-5-trifluoromethyl-2-pyridyloxy)-phenyl]-P,P-dimethyl-1-aminoethylphosphine oxide, and N-[2-nitro-5-(2-chloro-4-trifluoromethylphenoxy)-phenyl]-P,P-dimethyl-1-amino-2-(3-methylphenyl)-ethylphosphine oxide.

The compounds of the formula I are produced by reacting a dinitrophenylaryl ether of the formula II

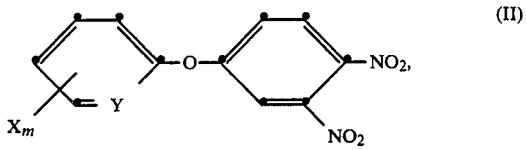

wherein X, Y and m have the meanings defined under the formula I, with an aminoalkylphosphine oxide derivative of the formula III

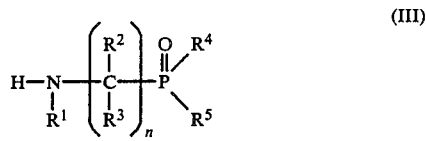

wherein $R^1$, $R^2$, $R^3$, $R^4$, $R^5$ and n have the meanings defined under the formula I.

The reaction to give compounds of the formula I is advantageously performed in an aprotic, inert organic solvent at a temperature of 50°–150° C., preferably between 70° and 120° C.

Suitable solvents are hydrocarbons, such as benzene, toluene, xylene or cyclohexane; ethers, such as ethylene glycol dimethyl ether, diethylene glycol dimethyl ether, tetrahydrofuran or dioxane; nitriles, such as acetonitrile, propionitrile; and dimethyl sulfoxide.

The starting compounds of the formulae II and III are known from the European Patent Specification No. 7471 and from G. M. Kosolapoff and L. Maier, Organic Phosphorus Compounds, Wiley Sons, New York, Vol. 3 (1976), respectively, or they can be produced by methods analogous to those given therein. Thus, for example, a novel compound of the formula III, P,P-dimethyl-aminomethylphosphine oxide, is obtained by an analogous method of the type mentioned.

The final products of the formula I according to the invention exhibit, in the case of both the pre- and the post-emergence application to weeds, an excellent herbicidal action. Cultivated plants are affected to only a slight extent or, with higher applied amounts, their growth is influenced. The compounds of the formula I are therefore suitable in a particular manner for the selective control of weeds in crops of productive plants, such as maize, soya bean, cotton and rice, and cereals, for example wheat, barley, rye and oats.

Furthermore, the active substances of the formula I are especially suitable for regulating plant growth.

The active substances of the formula I promote above all the root growth in cereal crops and the germination of plant seeds.

Some of the active substances according to the invention inhibit the growth of certain dicotyledonous plants, for example leguminosae planted as cover crops.

The invention hence relates also to herbicidal and plant-growth-regulating compositions containing a novel active ingredient of the formula I, and to processes for the pre- and post-emergence controlling to weeds and for regulating plant growth.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number or pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of high fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivative preferably contain 2 sulfonic acid groups and a fatty acid group having 8–22C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenyl-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"McCutcheon's Detergents and Emulsifiers Annual" MC Publishing Corp., Ridgewood, N.J., 1981; H. Stache, "Tensid-Taschenbuch" (Tenside Handbook), 2nd Edition, C. Hanser Verlag, Munich, Vienna, 1981; M and J. Ash, "Encyclopedia of Surfactants", Vol. I-III, Chemical Publishing Co., New York, 1980-1981.

The agrochemical preparations contain as a rule 0.1 to 99% especially 0.1 to 95% of active ingredient of the formula I, 1 to 99% of a solid or liquid additive, and 0 to 25%, particularly 0.1 to 25%, of a tenside.

Preferred formulations are made up in particular as follows (%=percent by weight):

| Solutions | | |
|---|---|---|
| active ingredient: | 5 to 95%, | preferably 10 to 80% |
| solvent: | 95 to 5%, | preferably 90 to 0% |
| surface-active agent: | 1 to 30%, | preferably 2 to 20%. |
| Emulsifiable concentrates | | |
| active ingredient: | 10 to 50%, | preferably 10 to 40% |
| surface-active agent: | 5 to 30%, | preferably 10 to 20% |
| liquid carrier: | 20 to 95%, | preferably 40 to 80%. |
| Dusts | | |
| active ingredient: | 0.5 to 10%, | preferably 2 to 8% |
| solid carrier: | 99.5 to 90%, | preferably 98 to 92%. |
| Suspension concentrates | | |
| active ingredient: | 5 to 75%, | preferably 10 to 50% |
| water: | 94 to 25%, | preferably 90 to 30% |
| surface-active agent: | 1 to 40%, | preferably 2 to 30%. |
| Wettable powders | | |
| active ingredient: | 5 to 90%, | preferably 10 to 80%, particularly 20 to 60% |
| surface-active agent: | 0.5 to 20%, | preferably 1 to 15% |
| solid carrier: | 5 to 90%, | preferably 30 to 70%. |
| Granulates | | |
| active ingredient: | 0.5 to 30%, | preferably 3 to 15% |
| solid carrier: | 99.5 to 70%, | preferably 97 to 85%. |

Whereas commercial products are preferably in the form of concentrated compositions, the preparations employed by the end-user are as a rule diluted. They can before application be diluted down to 0.001% of active ingredient. The applied amounts of active ingredient are usually 0.1 to 10 kg/ha, preferably 0.25 to 5 kg/ha.

The compositions can also contain further additives, such as stabilisers, antifoaming agents, viscosity regulators, binders and adhesives, as well as fertilisers or other active ingredients for obtaining special effects.

The Examples which follow serve to further illustrate the present invention.

PRODUCTION EXAMPLES

Example P1

N-[2-Nitro-5-(2-chloro-4-trifluoromethylphenoxy)-phenyl]-P,P-dimethyl-aminomethylphosphine oxide (compound No. 1.1)

A solution of 18.13 g of 3',4'-dinitro-2-chloro-4-trifluoromethyl-diphenyl ether in 50 ml of toluene is refluxed, and 10.71 g of melted P,P-dimethyl-aminomethylphosphine oxide are added dropwise, nitrous gases being formed in the course of the first half hour. The solution is refluxed for a further 2 hours and subsequently concentrated by evaporation. The residue is chromatographed with ethyl acetate/ethanol (4:1) on silica gel. The yield is 18.0 g (85% of theory) of N-[2-nitro-5-(2-chloro-4-trifluoromethylphenoxy)-phenyl]-P,P-dimethylaminomethylphosphine oxide in the form of yellow crystals, m.p. 166°–168° C.

Analysis: $C_{16}H_{15}ClF_3N_2O_4P$ (422.73) calculated: C 45.46%; H 3.58%; N 6.63%; F 13.48%; Cl 8.39%; P 7.33%. found: C 45.5%; H 3.6%; N 6.9%; F 13.4%; Cl 8.3%; P 7.5%.

Example P2

N-[2-Nitro-5-(5-trifluoromethyl-2-pyridyloxy)-phenyl]-P,P-dimethyl-aminomethylphosphine oxide (compound No. 1.2)

A solution of 4.97 g of (5-trifluoromethyl-2-pyridyloxy)-3,4-dinitrobenzene in 15 ml of toluene is refluxed, and 3.21 g of melted P,P-dimethyl-aminomethylphosphine oxide are added dropwise. The mixture is refluxed for a further 2 hours, nitrous gases being evolved at the start. The brown solution is subsequently concentrated by evaporation, and the residue is recrystallised from 50 ml of ethyl acetate to thus obtain 4.10 g (70% of theory) of N-[2-nitro-5-(5-trifluoromethyl-2-pyridyloxy)-phenyl]-P,P-dimethyl-aminomethylphosphine oxide in the form of yellow crystals, m.p. 158°–160° C.

Analysis: $C_{15}H_{15}F_3N_3O_4P$ (389.27). calculated: C 46.28%; H 3.89%; N 10.80%; F 14.64%; P 7.96%. found: C 46.0%; H 3.8%; N 10.8%; F 14.6%; P 8.0%.

Example P3

N-[2-Nitro-(3,5-dichloro-2-pyridyloxy)-phenyl]-P,P-dimethyl-aminomethylphosphine oxide (compound No. 1.3)

A solution of 4.95 g (3,5-Dichloro-2-pyridyloxy)-3,4-dinitrobenzene in 15 ml of toluene is refluxed, and 3.21 g of melted P,P-dimethyl-aminomethylphosphine oxide are added. After the initial evolution of nitrous gases has finished, the mixture is refluxed for a further 2 hours. The brown solution is subsequently concentrated by evaporation, and the residue is recrystallised from 20 ml of ethyl acetate and 100 ml of ether. There are obtained, in the form of yellow crystals, 4.9 g (84% of theory) of N-[2-nitro-5-(3,5-dichloro-2-pyridyloxy)-phenyl]-P,P-dimethyl-aminomethylphosphine oxide, m.p. 153°–155° C.

Analysis: $C_{14}H_{14}Cl_2N_3O_4P$ (390.16). calculated: C 43.10%; H 3.62%; N 10.77%; Cl 18.17%; P 7.94%. found: C 43.7%; H 3.6%; N 10.7%; Cl 17.8%; P 8.1%.

Example P4

P,P-Dimethyl-aminomethylphosphine oxide (a) N-Benzyl-P,P-dimethyl-aminomethylphosphine oxide A solution of 316.3 g of chloromethyl-dimethylphosphine oxide, 547 ml of benzylamine and 500 ml of ethanol is refluxed for 18 hours. After cooling to 20° to 25° C., the turbid suspension is filtered; the clear filtrate is then concentrated by evaporation, and to the residue are added 500 ml of 10% sodium chloride solution. The aqueous solution is extracted 4 times with 500 ml of methylene chloride each time; and the combined organic phases are subsequently dried over sodium sulfate and concentrated by evaporation. Vacuum distillation of the oily crude product yields 311.0 g (63% of theory) of N-benzyl-P,P-dimethyl-aminomethylphosphine oxide in the form of yellowish oil, b.p. 150° C./0.2 mb.

Analysis: $C_{10}H_{16}NOP$ (197.22). calculated: C 60.90%; H 8.18%; N 7.10%; P 15.71%. found: C 59.83%; H 8.03%; N 7.01%; P 15.83%.

(b) 148.0 g of N-benzyl-P,P-dimethyl-aminomethylphosphine oxide in 1.5 liters of ethanol are hydrogenated, with the addition of 45 g of 5% palladium/charcoal catalyst, in a hydrogen atmosphere. After the absorption of the calculated amount of hydrogen, the catalyst is separated, and the hydrogenated solution is concentrated by evaporation. Fractionation of the oily residue in vacuo yields 65.0 g (81% of theory) of P,P-dimethyl-aminomethylphosphine oxide in the form of colourless oil, which crystallises on standing for some time and is very hygroscopic, b.p. 89°–90° C./0.05 mb.

analysis: $C_3H_{10}NOP$ (107.09) calculated: C 33.65%; H 9.41%; N 13.08%; P 28.92%. found: C 33.26%; H 9.53%; N 12.89%; P 28.78%.

The compounds listed in the following Tables are otained in an analogous manner:

TABLE 1

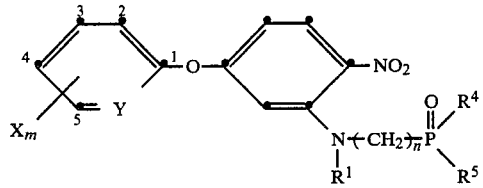

| Comp. No. | $X_m$ | Y | $R^1$ | $R^4$ | $R^5$ | n | Physical data |
|---|---|---|---|---|---|---|---|
| 1.1 | 2-Cl, 4-CF$_3$ | CH | H | CH$_3$ | CH$_3$ | 1 | m.p. 166–168° C. |
| 1.2 | 4-CF$_3$ | N | H | CH$_3$ | CH$_3$ | 1 | m.p. 158–160° C. |
| 1.3 | 2-Cl, 4-Cl | N | H | CH$_3$ | CH$_3$ | 1 | m.p. 153–155° C. |
| 1.4 | 2-Cl, 4-Cl | N | H | C$_2$H$_5$ | C$_2$H$_5$ | 1 | |
| 1.5 | 2-Cl, 4-CF$_3$ | N | H | CH$_3$ | CH$_3$ | 1 | |
| 1.6 | 2-Cl, 4-CF$_3$ | N | H | C$_2$H$_5$ | C$_2$H$_5$ | 1 | |
| 1.7 | 2-Cl, 4-CF$_3$ | N | H | C$_3$H$_7$—i | C$_3$H$_7$—i | 1 | |
| 1.8 | 2-Cl, 4-CF$_3$ | N | H | CH$_3$ | C$_3$H$_7$—i | 1 | |
| 1.9 | 2-Cl, 4-CF$_3$ | CH | H | C$_2$H$_5$ | C$_2$H$_5$ | 1 | m.p. 79–81° C. |
| 1.10 | 2-Cl, 4-CF$_3$ | CH | H | C$_3$H$_7$—i | C$_3$H$_7$—i | 1 | |
| 1.11 | 2-Cl, 4-CF$_3$ | CH | H | CH$_3$ | C$_3$H$_7$—i | 1 | |
| 1.12 | 2-Cl, 6-Cl, 4-CF$_3$ | CH | H | CH$_3$ | CH$_3$ | 1 | |
| 1.13 | 2-Cl, 6-Cl, 4-CF$_3$ | CH | H | C$_2$H$_5$ | C$_2$H$_5$ | 1 | |
| 1.14 | 2-Cl, 4-Cl | N | H | C$_3$H$_7$—i | C$_3$H$_7$—i | 1 | |
| 1.15 | 2-Cl, 4-Cl | CH | H | C$_3$H$_7$—i | C$_3$H$_7$—i | 1 | |
| 1.16 | 2-Cl, 4-Cl | CH | H | CH$_3$ | CH$_3$ | 1 | |
| 1.17 | 2-Cl, 4-CF$_3$ | CH | H | C$_3$H$_7$—n | C$_3$H$_7$—n | 1 | |
| 1.18 | 2-Cl, 4-CF$_3$ | CH | H | C$_4$H$_9$—n | C$_4$H$_9$—n | 1 | |
| 1.19 | 2-Cl, 4-CF$_3$ | CH | CH$_3$ | CH$_3$ | CH$_3$ | 1 | |
| 1.20 | 2-Cl, 4-CF$_3$ | CH | C$_2$H$_5$ | CH$_3$ | CH$_3$ | 1 | |
| 1.21 | 2-Cl, 4-CF$_3$ | CH | CH$_2$C$_6$H$_5$ | CH$_3$ | CH$_3$ | 1 | |
| 1.22 | 2-Cl, 4-CF$_3$ | CH | CH$_2$C$_6$H$_5$ | C$_2$H$_5$ | C$_2$H$_5$ | 1 | |
| 1.23 | 2-Cl, 4-CF$_3$ | CH | H | C$_2$H$_5$ | C$_2$H$_5$ | 2 | |
| 1.24 | 2-Cl, 4-CF$_3$ | CH | H | C$_2$H$_5$ | C$_2$H$_5$ | 2 | |

TABLE 1-continued

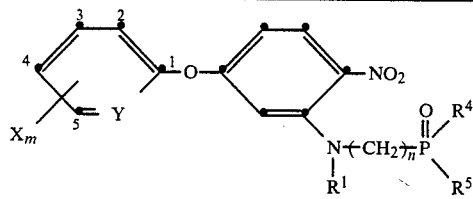

| Comp. No. | $X_m$ | Y | $R^1$ | $R^4$ | $R^5$ | n | Physical data |
|---|---|---|---|---|---|---|---|
| 1.25 | 2-Cl, 4-CF$_3$ | CH | H | CH$_3$ | CH$_3$ | 2 | |
| 1.26 | 2-Cl, 4-CF$_3$ | CH | H | CH$_3$ | CH$_3$ | 2 | |
| 1.27 | 2-Cl, 4-CF$_3$ | CH | C$_3$H$_7$—n | CH$_3$ | CH$_3$ | 1 | resin |

TABLE 2

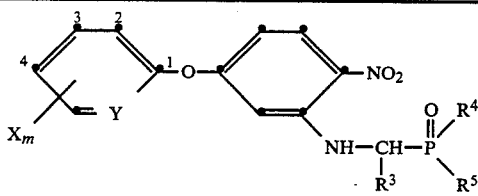

| Comp. No. | $X_m$ | Y | $R^3$ | $R^4$ | $R^5$ | Physical data |
|---|---|---|---|---|---|---|
| 2.1 | 2-Cl, 4-CF$_3$ | CH | CH$_3$ | CH$_3$ | CH$_3$ | m.p. 151–153° C. |
| 2.2 | 2-Cl, 4-CF$_3$ | N | CH$_3$ | CH$_3$ | CH$_3$ | m.p. 180–181° C. |
| 2.3 | 2-Cl, 4-CF$_3$ | CH | CH$_3$ | C$_2$H$_5$ | C$_2$H$_5$ | |
| 2.4 | 2-Cl, 4-CF$_3$ | N | CH$_3$ | C$_2$H$_5$ | C$_2$H$_5$ | |
| 2.5 | 2-Cl, 4-CF$_3$ | CH | 3-CH$_3$—C$_6$H$_4$—CH$_2$— | CH$_3$ | CH$_3$ | m.p. 161–165° C. |
| 2.6 | 2-Cl, 4-CF$_3$ | N | 3-CH$_3$—C$_6$H$_4$—CH$_2$— | CH$_3$ | CH$_3$ | |

FORMULATION EXAMPLES

Example F1

Formulation Examples for liquid active ingredients of the formula I (%=percent by weight)

| (a) Emulsion concentrates | (a) | (b) | (c) |
|---|---|---|---|
| active ingredient | 20% | 40% | 50% |
| calcium dodecylbenzene sulfonate | 5% | 8% | 5.8% |
| castor oil polyethylene glycol ether (36 mols of ethylene oxide) | 5% | — | — |
| tributylphenoyl-polyethylene glycol ether (30 mols of ethylene oxide) | — | 12% | 4.2% |
| cyclohexanone | — | 15% | 20% |
| xylene mixture | 70% | 25% | 20% |

Emulsions of any desired concentration can be obtained from these concentrates by dilution with water.

| (b) Solutions | (a) | (b) | (c) | (d) |
|---|---|---|---|---|
| active ingredient | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | 1% | 5% |
| epoxidised coconut oil | — | — | 94% | — |

The solutions are suitable for application in the form of very fine droplets.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride; the solution is sprayed onto the carrier, and the solvent is subsequently evaporated off in vacuo.

| (d) Dusts | (a) | (b) |
|---|---|---|
| active ingredient | 2% | 5% |
| highly dispersed silicic acid | 1% | 5% |
| talkum | 97% | — |
| kaolin | — | 90% |

Dusts ready for use are obtained by mixing the active-ingredient with the carriers, and grinding the mixture in a suitable mill.

Example F2

Formulation Examples for solid active ingredients of the formula I (%=percent by weight)

| (a) Wettable powders | (a) | (b) |
|---|---|---|
| active ingredient | 20% | 60% |
| sodium lignin sulfonate | 5% | 5% |
| sodium lauryl sulfate | 3% | 6% |
| octylphenolpolyethylene glycol ether (7-8 mols of ethylene oxide) | — | 2% |
| highly dispersed silicic acid | 5% | 27% |
| kaolin | 67% | — |

The active ingredient is well mixed with the additives and the mixture is ground in a suitable mill. There are obtained wettable powders which can be diluted with water to give suspensions of the concentration required.

| (b) Emulsion concentrate | |
|---|---|
| active ingredient | 10% |
| octylphenolpolyethylene glycol ether (4-5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| (c) Dusts | (a) | (b) |
|---|---|---|
| active ingredient | 5% | 8% |
| talcum | 95% | — |
| kaolin | — | 92% |

Dusts ready for use are obtained by mixing the active ingredient with the carriers, and grinding the mixture in a suitable mill.

| (d) Extruder granulate | |
|---|---|
| active ingredient | 10% |
| sodium lignin sulfonate | 2% |
| carboxymethylcellulose | 1% |
| kaolin | 87% |

The active ingredient is mixed with the additives, and the mixture is then ground and moistened with water. The mixture is extruded and subsequently dried in a stream of air.

| (e) Coated granulate | |
|---|---|
| active ingredient | 3% |
| polyethylene glycol (M.W. 200) | 3% |
| kaolin | 94% |

The finely ground active ingredient is uniformly applied, in a mixer, to the kaolin moistened with polyethylene glycol. Dustfree coated granules are obtained in this manner.

| (f) Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

BIOLOGICAL EXAMPLES

Example B1

Verification of the herbicidal activity before emergence of the plants

Plant seeds are sown in flower pots (12-15 cm diameter) in a greenhouse. The surface of the soil is treated immediately afterwards with an aqueous dispersion or solution of the active ingredients, the concentration used being 4 kg of active ingredient per hectare. The pots are then kept in the greenhouse at a temperature of 22°-25° C. with 50-70% relative humidity. The test results are evaluated after 3 weeks, and the action on the test plants is assessed according to the following scale of ratings:

| | |
|---|---|
| 1 | plants have not emerged or are totally destroyed |
| 2-3 | very strong action |
| 4-6 | medium action |
| 7-8 | weak action |
| 9 | no action (as untreated control plants). |

PRE-EMERGENCE ACTION

Applied amount: 4 kg of active ingredient/hectare

| Comp. No. | Avena | Setaria | Sinapis | Stellaria |
|---|---|---|---|---|
| 1.1 | 2 | 2 | 1 | 1 |
| 1.2 | 8 | 9 | 7 | 4 |
| 1.3 | 2 | 1 | 1 | 2 |
| 1.9 | 2 | 1 | 1 | 1 |
| 1.27 | 9 | 2 | 2 | 1 |
| 2.1 | 2 | 1 | 1 | 1 |

Example B2

Verification of the herbicidal activity after emergence of the plants

A number of weeds and cultivated plants, both monocotyledons and dicotyledons, are sprayed, after emergence, in the 4- to 6-leaf stage with an aqueous active-ingredient dispersion in dosages of 4 kg of active ingredient per hectare, and are then kept at 24° to 26° C. with 45-60% relative humidity. The test results are evaluated 15 days after the treatment, and an assessment is made according to the scale of ratings used in the pre-emergence test.

POST-EMERGENCE ACTION

Applied amount: 4 kg of active ingredient per hectare

| Comp. No. | Avena | Setaria | Lolium | Solanum | Sinapis | Stellaria | Phaseolus |
|---|---|---|---|---|---|---|---|
| 1 | 2 | 2 | 5 | 1 | 1 | 2 | 1 |
| 2 | 4 | 6 | 7 | 4 | 2 | 4 | 6 |
| 3 | 3 | 4 | 3 | 1 | 2 | 4 | 2 |
| 1.9 | 1 | 2 | 2 | 1 | 1 | 2 | 9 |
| 1.27 | 2 | 1 | 3 | 1 | 1 | 2 | 2 |
| 2.1 | 1 | 1 | 2 | 1 | 1 | 1 | 2 |

What is claimed is:

1. A (2-nitro-5-aryloxy-phenylamino)-alkylphosphine oxide derivative of the formula

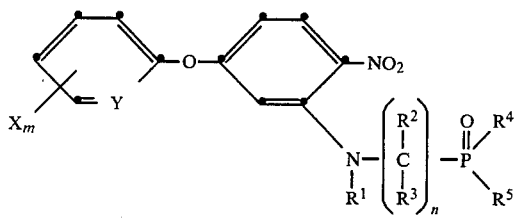

wherein

X is halogen or $CF_3$,

Y is nitrogen or —CH=, $R^1$ is hydrogen, $C_1$-$C_4$-alkyl, or aralkyl having 1–4 carbon atoms in the alkyl moiety, $R^2$ is hydrogen or $C_1$-$C_4$-alkyl, $R^3$ is hydrogen, $C_1$-$C_4$-alkyl, phenyl, benzyl or $C_1$-$C_4$-alkylbenzyl, $R^4$ and $R^5$ independently of one another are each $C_1$-$C_4$-alkyl, $C_1$-$C_4$-haloalkyl, $C_2$-$C_6$-alkoxyalkyl, or aralkyl having 1–4 carbon atoms in the alkyl moiety, m is zero to 3, and n is 1 to 3.

2. A compound according to claim 1, wherein m is 2.

3. A compound according to claim 1, wherein X is trifluoromethyl or chlorine.

4. A compound according to claim 1, wherein $R^1$ is hydrogen.

5. A compound according to claim 1, wherein $R^4$ is $C_1$-$C_4$-alkyl.

6. A compound according to claim 1, wherein $R^5$ is $C_1$-$C_4$-alkyl.

7. A compound according to claim 1, wherein Y is the —CH= group, m is 2, the two X groups are chlorine in the 2-position and trifluoromethyl in the 4-position, respectively, $R^1$ is hydrogen, and $R^4$ and $R^5$ independently of one another are each $C_1$-$C_4$-alkyl.

8. A compound according to claim 1, wherein Y is nitrogen, m is 1 and X is trifluoromethyl in the 5-position, $R^1$ is hydrogen, and $R^4$ and $R^5$ independently of one another are each $C_1$-$C_4$-alkyl.

9. A compound according to claim 7, of the formula

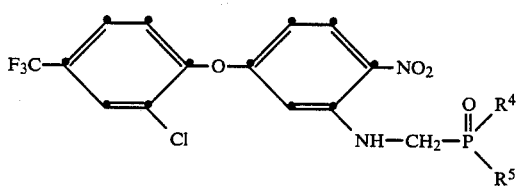

wherein $R^4$ and $R^5$ independently of one another are each methyl or ethyl.

10. A compound according to claim 1, of the formula

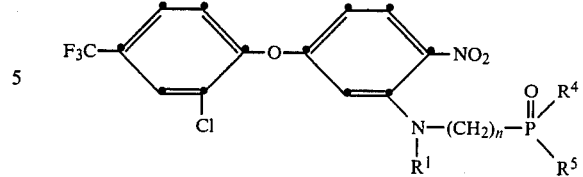

wherein $R^1$ is hydrogen, methyl, ethyl, propyl or benzyl, $R^4$ and $R^5$ independently of one another are each $C_1$-$C_4$-alkyl.

11. A compound according to claim 7, of the formula

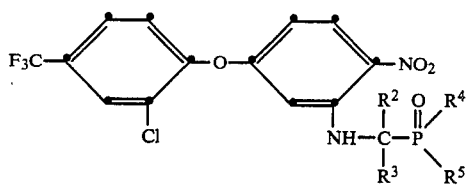

wherein $R^2$ is methyl, $R^3$ is hydrogen or methyl, $R^4$ and $R^5$ independently of one another are each methyl or ethyl.

12. N-[2-Nitro-5-(2-chloro-4-trifluoromethylphenoxy)-phenyl]-P,P-dimethylaminomethylphosphine oxide according to claim 1.

13. N-[2-Nitro-5-(5-trifluoromethyl-2-pyridyloxy)-phenyl]-P,P-dimethylaminomethylphosphine oxide according to claim 1.

14. N-[2-Nitro-5-(3,5-dichloro-2-pyridyloxy)-phenyl]-P,P-dimethylaminomethylphosphine oxide according to claim 1.

15. N-[2-Nitro-5-(2-chloro-4-trifluoromethylphenoxy)-phenyl]-P,P-diethylaminomethylphosphine oxide according to claim 1.

16. N-[2-Nitro-5-(2-chloro-4-trifluoromethylphenoxy)-phenyl]-P,P-dimethyl-1-aminobutylphosphine oxide according to claim 1.

17. N-[2-Nitro-5-(2-chloro-4-trifluoromethylphenoxy)-phenyl]-P,P-dimethyl-1-aminoethylphosphine oxide according to claim 1.

18. N-[2-Nitro-5-(3-chloro-5-trifluoromethyl-2-pyridyloxy)-phenyl]-P,P-dimethyl-1-aminoethylphosphine oxide according to claim 1.

19. N-[2-Nitro-5-(2-chloro-4-trifluoromethylphenoxy)-phenyl]-P,P-dimethyl-1-amino-2-(3-methylphenyl)-ethylphosphine oxide according to claim 1.

20. A herbicidal or plant-growth-regulating composition which comprises, as active ingredient, a compound of according to claim 1 in combination with a suitable carrier.

21. A method of controlling undesirable plant growth or for regulating plant growth, which method comprises applying to plants, to the locus thereof or to parts of plants an effective amount of a compound of claim 1.

22. A method of claim 21 for controlling weeds in crops of cultivated plants.

23. A method of claim 21 for controlling weeds in crops of maize, soya-bean, cotton, rice or cereals.

24. A method of claim 23 for controlling dicotyledonous weeds.

25. A method of claim 23 for controlling monocotyledonous weeds in rice crops.

26. A method of claim 21 for promoting the root growth of cereal plants.

* * * * *